(12) United States Patent
Dunkel

(10) Patent No.: US 6,241,134 B1
(45) Date of Patent: Jun. 5, 2001

(54) APPARATUS AND METHOD FOR THE REMOVAL OF GLOVES

(76) Inventor: David Dunkel, 1682 Thurston Dr., Laguna Beach, CA (US) 92651

( * ) Notice: Subject to any disclaimer, the term of this patent is extended or adjusted under 35 U.S.C. 154(b) by 0 days.

(21) Appl. No.: 09/158,645

(22) Filed: Sep. 22, 1998

(51) Int. Cl.[7] .................................................. A47G 25/90
(52) U.S. Cl. ................................................................ 223/111
(58) Field of Search .................................... 223/111, 117, 223/118, 112

(56) References Cited

U.S. PATENT DOCUMENTS

| | | |
|---|---|---|
| 1,163,399 * | 12/1915 | Fox ........................................ 223/119 |
| 1,271,069 * | 7/1918 | Orr ........................................ 223/119 |
| 3,805,297 | 4/1974 | Margolis . |
| 4,876,747 | 10/1989 | Coffey et al. . |
| 4,893,955 | 1/1990 | Zielinski . |
| 4,915,226 | 4/1990 | Keenan . |
| 4,942,992 | 7/1990 | Fischer et al. . |
| 4,971,233 | 11/1990 | Keenan . |
| 5,152,439 * | 10/1992 | Simons ................................. 223/114 |
| 5,224,220 | 7/1993 | Andriola . |
| 5,365,608 | 11/1994 | Flick . |
| 5,405,066 * | 4/1995 | Fakier ................................... 223/111 |
| 5,467,483 | 11/1995 | Saadatmanesh et al. . |
| 5,566,394 | 10/1996 | Flick . |
| 5,579,539 | 12/1996 | Flick . |
| 5,675,839 | 10/1997 | Gordon et al. . |
| 5,894,970 * | 4/1999 | Belkin et al. ........................ 223/112 |

\* cited by examiner

*Primary Examiner*—Bibhu Mohanty
(74) *Attorney, Agent, or Firm*—Lyon & Lyon LLP

(57) ABSTRACT

The invention is directed to a novel apparatus and method for removing gloves including a glove removal member. When a glove wearer inserts the glove removal member between the a glove and the wearer's hand or forearm, and the portions of the apparatus cooperate to remove the glove from the wearer's hand as the wearer's hand moves in a direction away from the apparatus.

11 Claims, 5 Drawing Sheets

APPARATUS AND METHOD FOR THE REMOVAL OF GLOVES

BACKGROUND

1. Field of the Invention

This invention relates generally to apparatuses and methods for the removal of gloves. The apparatus allows a wearer to remove a glove and dispose of it in one step. The apparatus may also be used to prevent contact or cross-contamination of the outer surface of the glove with the wearer or other personnel.

2. Related Art

Protective gloves are commonly used for activities where it is desired to provide a barrier between the wearer and the material handled by the wearer. For convenience and safety, disposable protective gloves are generally used to prevent contamination from one use to the next. One traditional use of gloves has been to maintain a sterile interface between a surgeon and patient. More commonly now, gloves are used to isolate the wearer from a material the wearer handles, especially when there is potential for contact with infectious, hazardous, offensive, undesirable or harmful material. For example, latex elastomeric gloves are worn routinely by dentists, surgeons, paramedics, laboratory technicians, hazardous waste handlers, automotive mechanics, sports trainers, law enforcement personnel and the like in the performance of their job duties to avoid contact with the material.

Close fitting protective gloves are typically used so as not to impair a wearer's tactile sense, a necessity in procedures in areas as diverse as surgery and auto mechanics. These gloves are often constructed of thin gauge elastomeric material, such as latex or natural rubber so as to stretch around and intimately conform to the shape of the human hand. These properties allow a wearer a relatively unimpaired sense of feel while maintaining a barrier between the wearer and the material being handled. As with any gloves, typically a wearer will don the gloves by, in succession, grasping the cuff of a glove with the fingers of one hand and pulling it over the fingers and hand of the other.

During the many procedures in which protective gloves are used, the exterior surface may become contaminated with an infectious or hazardous material being handled. Although the wearer is protected from contact with the material while the gloves are on the hands of the wearer, during glove removal the wearer may potentially come into contact with the material. With most commercially available gloves, to remove a first glove, a wearer must use a second gloved hand to assist in the removal of the first glove. Typically the wearer places at least one finger of the second gloved hand under the cuff of the first glove near the wrist or forearm of the wearer, grasps the cuff of the first glove, and pulls the first glove away from the wearer's hand. The second glove is removed in the same manner, except the wearer uses an ungloved hand to grasp the second glove and remove it. The close conforming fit of thin gauge elastomeric gloves makes the removal of gloves especially difficult.

When the first glove is contaminated, the skin around or above the cuff of the second glove may become contaminated, for example, from the finger portion of the contaminated first glove. Additionally, the first hand may become contaminated, for example, when grasping the cuff or other portion of the second glove and removing it. Thus, when protective gloves are used with infectious, hazardous or undesirable material, there is a risk of physical contact between the wearer and the material during removal of the gloves, especially when one hand is used to assist in the removal of a glove from the opposite hand. Alternatively, if another person assists the wearer with glove removal, there is a risk of cross-contamination between the wearer's glove and the other person.

In the past, there have been attempts to assist in the removal of a wearer's glove. There have also been attempts to limit the cross-contamination between the exterior surface of the gloves of a wearer and the wearer, or others, during glove removal by modifications to the glove itself. For example, U.S. Pat. No. 4,876,747 to Coffey describes a glove with a raised loop. In U.S. Pat. Nos. 5,579,539, 5,566,394, and 5,365,608, Flick describes a disposable elastomeric glove having a protuberance. In U.S. Pat. No. 5,467,483, Saadatmanesh describes a glove having a wrist portion that contains a removable protective cover over a gripping means.

While some of the known protective gloves reportedly help in preventing cross-contamination between contaminated gloves and the wearer during removal, these gloves are necessarily more difficult to manufacture and complicated to use. Additionally, these known gloves with modifications designed to assist in their removal are more expensive to manufacture and more expensive for the consumer than the commonly available thin gauge elastomeric latex gloves. Further, the known gloves with modifications to assist in their removal are not as readily available as the standard elastomeric latex gloves without modifications. Therefore, there exists a need for an apparatus that will aid a wearer in the removal of commercially available elastomeric latex gloves that are potentially contaminated or known to be contaminated. Additionally, there exists a need for an apparatus suitable for any application where a glove wearer desires to easily remove a glove without the assistance of the wearer's opposite hand or another person.

SUMMARY

The glove removal apparatus and method of the present invention, in certain embodiments, allows a wearer to remove a glove with a potentially contaminated exterior surface and dispose of it in one step, and thereby substantially decreases the risk of cross-contamination between the exterior surface of the glove and the wearer or other personnel. It is an object of the present invention to overcome the drawbacks of the prior art. Other objects and advantages of the present invention will become apparent from the following detailed description of the preferred embodiments taken in conjunction with the accompanying drawings.

DETAILED DESCRIPTION

The present invention is directed to an apparatus and method for removing gloves. Various embodiments of the apparatus will first be described, followed by a discussion of the invention in operation (shown in FIG. 3).

Figure 1:
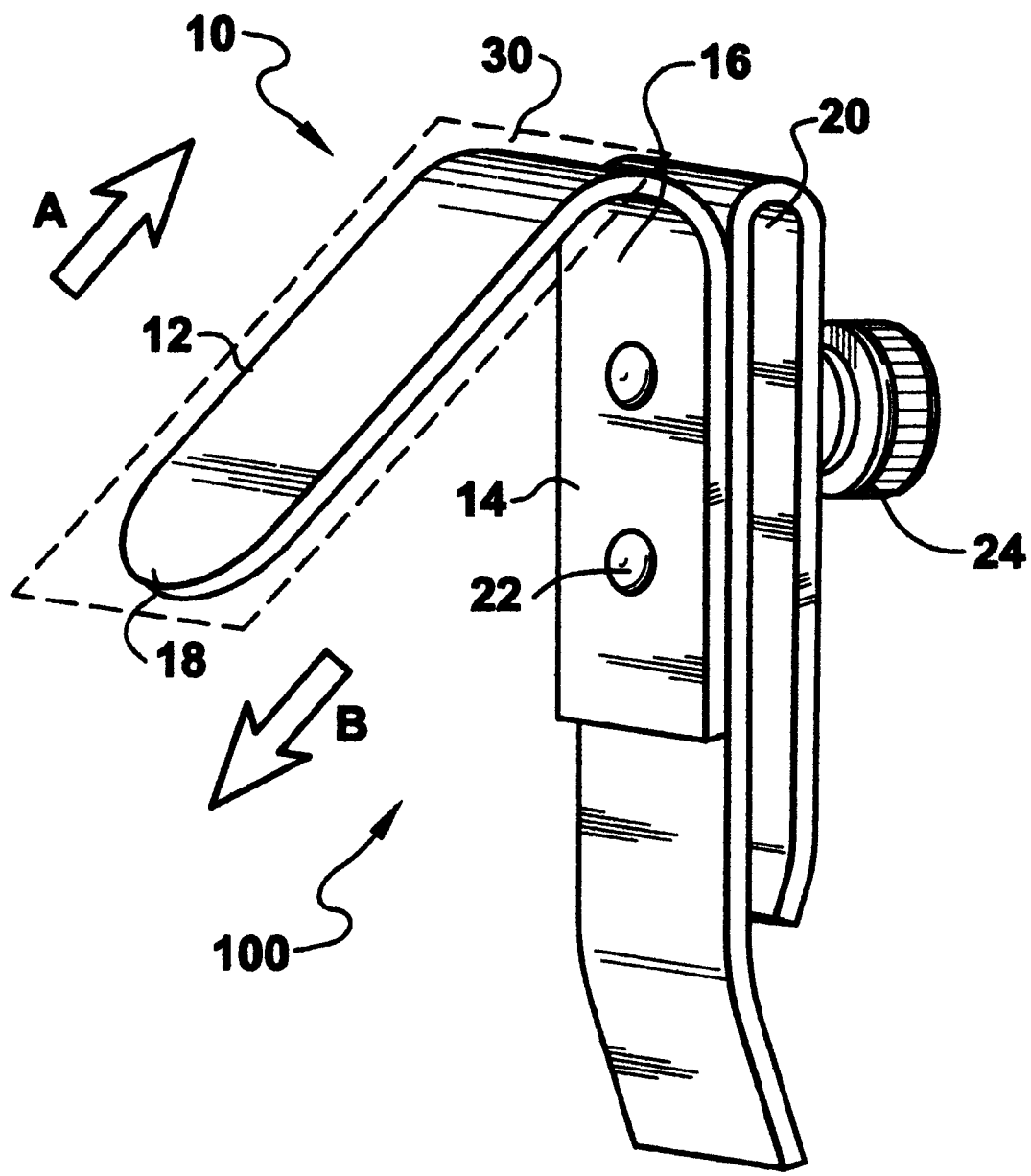
FIG. 1 is a perspective view of one embodiment of the present invention.
Figure 2:
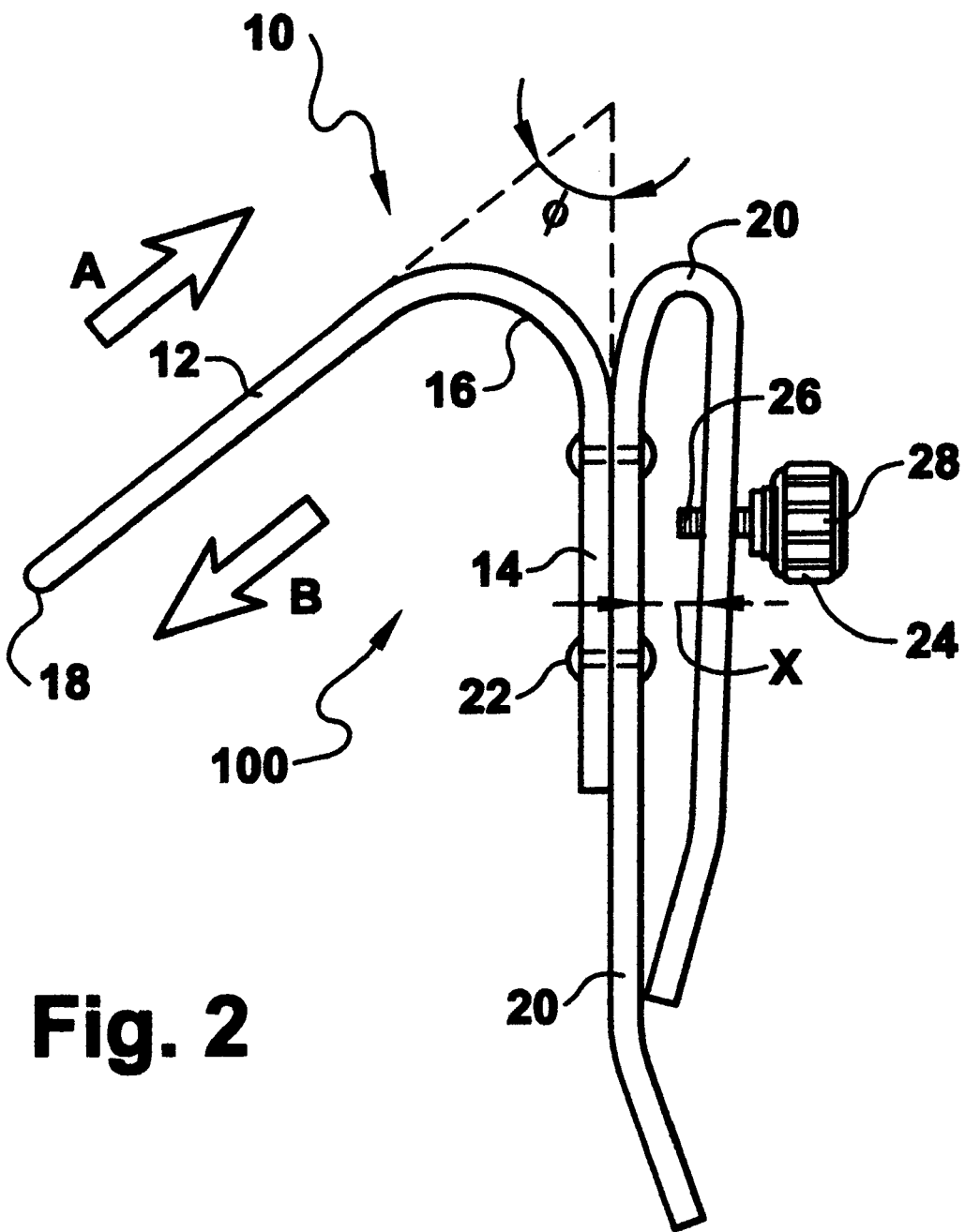
FIG. 2 is a side view of the embodiment of FIG. 1.
Figure 3:
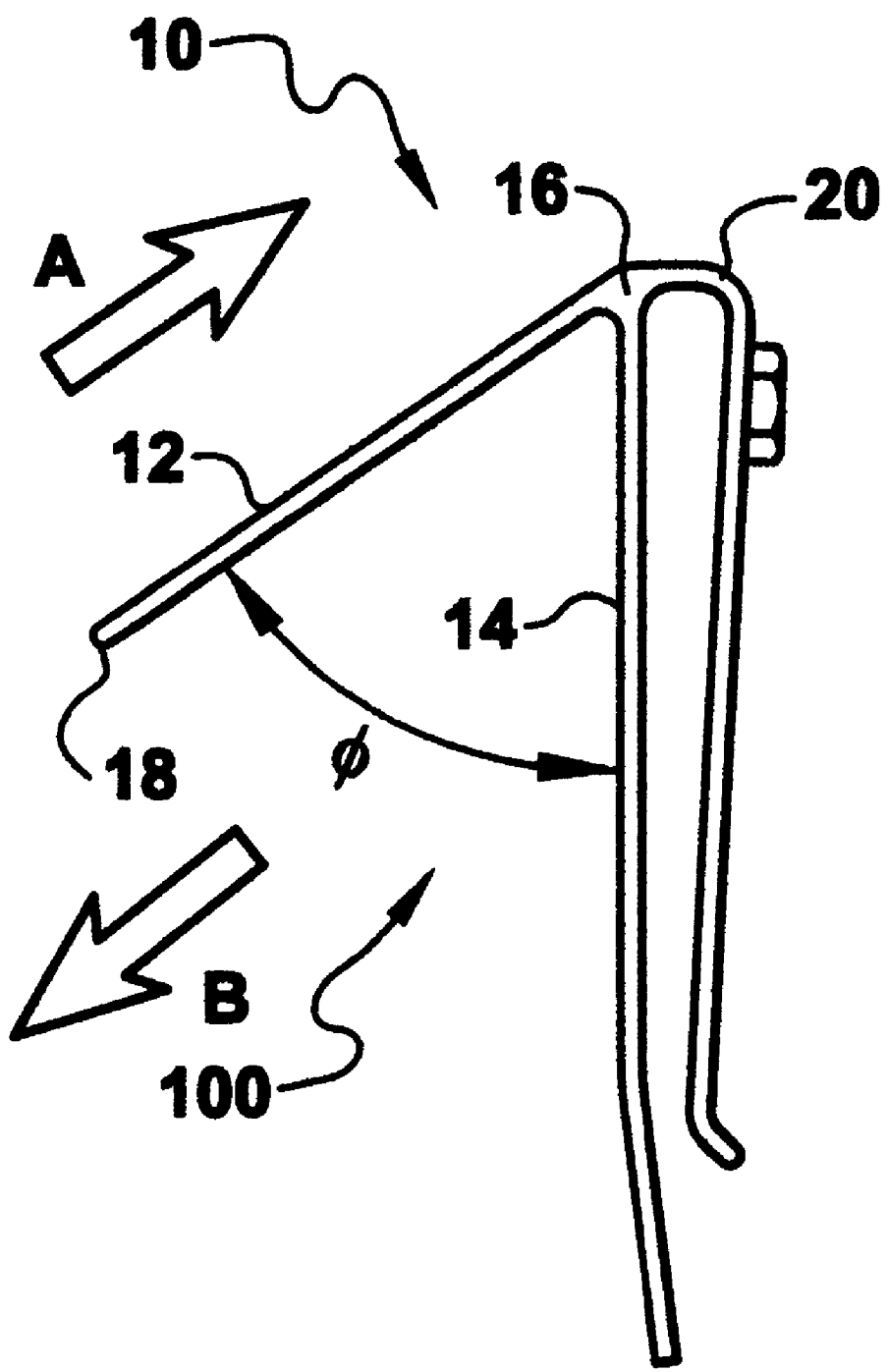
FIG. 3 is a side view of another embodiment of the invention.

Referring to FIGS. 1, 2 and 3, there are shown embodiments of the glove removal apparatus of the present invention generally depicted by numeral 100. Apparatus 100 includes member 10. At one end of the member 10 is a first end portion 18. First end portion 18 is adjacent to a middle portion 12. A second end portion 14 of member 10 is connected to the middle portion 12 through a bent portion 16 forming an angle $\phi$ from the intersection of the planes from middle portion 12 and the second end portion 14. Second end portion 14 of member 10 may be attached through a connector 22 to a holding portion 20 optionally comprising a securer 24. Securer 24 of holding portion 20 is optionally comprised of a screw portion 26 and knob portion 28, wherein knob portion 28 may be turned so that screw portion 26 is securely attached to a stationary object. Sleeve 30 is optionally placed on member 10.

Variations in portions of the glove removal apparatus 100 of the present invention constitute additional embodiments of the present invention and will be apparent to those skilled in the art to assist in the removal of a glove from a wearer. For example, the glove removal apparatus 100 of the present invention may be comprised of one piece or a plurality of pieces. In one embodiment of the invention, the glove removal apparatus of the present invention 100 is comprised of a plurality of pieces, for example, one piece comprising member 10, including first end portion 18, middle portion 12, bent portion 16 and second end portion 14, and a second piece comprising holding portion 20. Preferably, the glove removal apparatus 100 of the present invention is comprised of one piece as in, for example, FIG. 3. In one preferred embodiment, the one piece is comprised of first end portion 18, middle portion 12, bent portion 16 and second end portion 14 of member 10. In a more preferred embodiment, the one piece is comprised of first end portion 18, middle portion 12, bent portion 16 and second end portion 14 of member 10, and holding portion 20.

Additionally, the glove removal apparatus of the present invention may be of uniform or varying thickness and width throughout the different portions of the apparatus. The thickness and width of the glove removal apparatus 100 and, in particular, middle portion 12 and first end portion 18 of member 10, is of optimal size for fitting in a depression in the middle of the palm of a glove wearer's hand and the surfaces finished so that the apparatus does not rip the wearer's glove during glove removal. The thickness and width of member 10 are of sufficient dimensions to provide stability to the apparatus 100 as well as fit between a glove and palm of the wearer during glove removal. Preferably, member 10 is of uniform thickness and width from middle portion 12 through bent portion 16 and second end portion 14.

In one embodiment of the invention, first end portion 18 is curved on its outer edge in varying degrees to assist in fitting between the cuff portion of a wearer's glove and the wearer's wrist or forearm. In another embodiment of the invention, the outer edges of first end portion 18 taper together from middle portion 12 and meet together to substantially form a point. In yet another embodiment of the invention, the outer edges of first end portion 18 continue straight from middle portion 12 and form two angles of about 90° at the outer edge of first end portion 18. First end portion 18 fits comfortably between the glove of a wearer and the crease between a lower part of a wearer's thumb and an outer part of a wearer's hand during the glove removal process. Preferably, first end portion 18 is uniformly curved on an outer edge of first end portion 18 towards the edges of middle portion 12 and extends about 1 cm past middle portion 12. Preferably, first end portion 18 and middle portion 12 are pointed downward so that during the glove removal process, when a glove is dislodged from a wearer's hand with the assistance of the glove removal apparatus 100, the glove springs off in a downward direction B.

As may be appreciated by reference to FIGS. 1, 2 and 3, middle portion 12 is substantially more flat than bent portion 16. In one embodiment of the invention, middle portion 12 may be slightly curved upwards or downwards extending from bent portion 16 to first end portion 18. Additionally, middle portion 12 may have a plurality of depressional or elevational features along an exterior surface to aid in the glove removal process. In a preferred embodiment of the invention, middle portion 12 is substantially flat with a uniformly smooth surface extending from bent portion 16 to first end portion 18.

Bent portion 16 is a region of member 10 formed between middle portion 12 and second end portion 14 so as to form an angle $\phi$ from the intersection of the plane of middle portion 12 with the plane of second end portion 14. The angle $\phi$ is of optimal degree to allow the glove of a wearer to spring off during the process of glove removal. The angle $\phi$ in bent portion 16 will vary depending upon the particular application of the glove removal apparatus and the desired trajectory of the glove being removed.

Referring again to FIG. 1, in an alternative embodiment of the invention a sleeve 30 is used with member 10, fitting over any portion, or all, of first end portion 18, middle portion 12 and bent portion 16. In a preferred embodiment of the invention, a plastic sleeve 30 is used to fit over first end portion 18, middle portion 12 and part of bent portion 16 of apparatus 10. The plastic sleeve may be comprised of an appropriate polymer or plastic which will be apparent to those skilled in the art.

As will be appreciated by reference to FIGS. 1, 2 and 3, second end portion 14 is slightly curved or substantially flat compared with bent portion 16, extending away from bent portion 16. Preferably, second end portion 14 is substantially flat compared with bent portion 16. Second end portion 14 is of a length sufficient to attach apparatus 100 to a stationary object or holding portion 20 so that apparatus 100 is held substantially stationary during the glove removal process. In one embodiment of the invention, member 10 is attached directly to a stationary object at second end portion 14. In a preferred embodiment, member 10 is connected to a holding portion 20 at second end portion 14, wherein holding portion 20 is attached to a stationary object.

In some embodiments of the invention, second end portion 14 further comprises a connector 22 for attaching member 10 to a stationary object or to a holding portion 20. Thus, member 10 is attached to a stationary object or holding portion at second end portion 14 by connector 22, wherein connector 22 comprises a means for securing member 10 to a stationary object or holding portion 20. Variations in connector 22 sufficient to connect member 10 at second end portion 14 to a stationary object or to holding portion 20 constitute additional embodiments of the invention and will be apparent to those skilled in the art. Such embodiments may include an adhesive on a surface or part thereof of second end portion 14 facing away from middle portion 12, rivets, screws, nails, hook and loop, and the like, or any combination thereof in at least one position on second end portion 14. In a preferred embodiment of the invention, member 10 is attached to a holding portion 20 at second end portion 14 by connector 22, comprising two rivets, each located about equidistant from the center and one end of second end portion 14.

In embodiments of the present invention comprising a holding portion 20, holding portion 20 and second end portion 14 are of a sufficient shape and size for attaching to a stationary object so that member 10 remains substantially secure during the process of glove removal. In other embodiments of the invention, the size and shape of holding portion 20 and second end portion 14 are designed based on the trajectory required for disposing a glove into a disposal container during the glove removal process.

In a preferred embodiment of the invention, holding portion 20 is of the same uniform width and thickness as middle portion 12, bent portion 16 and second end portion 14 of member 10. In some embodiments of the invention, the shape of holding portion 20 is formed by a first end of holding portion 20 bent back at about the middle of holding portion 20 so that the first end of holding portion 20 is near the second end of holding portion 20 by a sufficient distance x so that holding portion 20 may fit over a portion of a stationary object such as the lip of a waste receptacle.

In embodiments of the invention that comprise holding portion 20, holding portion 20 may be secured to a stationary object by means of tension, friction-fit or a spring-like action caused by formation of the first and second ends of holding portion 20 or between holding portion 20 and second end portion 14 as in, for example, FIGS. 1, 2 and 3. In alternative embodiments of the invention that comprise holding portion 20, holding portion 20 further comprises a securer 24 for attaching to a stationary object. Variations in securer 24 sufficient to attach holding portion 20 to a stationary object constitute additional embodiments of the invention and will be apparent to those skilled in the art. Such embodiments comprise an adhesive on a surface or part thereof of holding means 20, rivets, screws, nails, hook and loop, and the like, or any combination thereof in at least one position of holding portion 20.

In a preferred embodiment of the invention, securer 24 is comprised of a screw portion 26 optionally and a knob portion 28, wherein knob portion 28 is turned so that screw portion 26 is securely attached to a stationary object.

Figure 4:
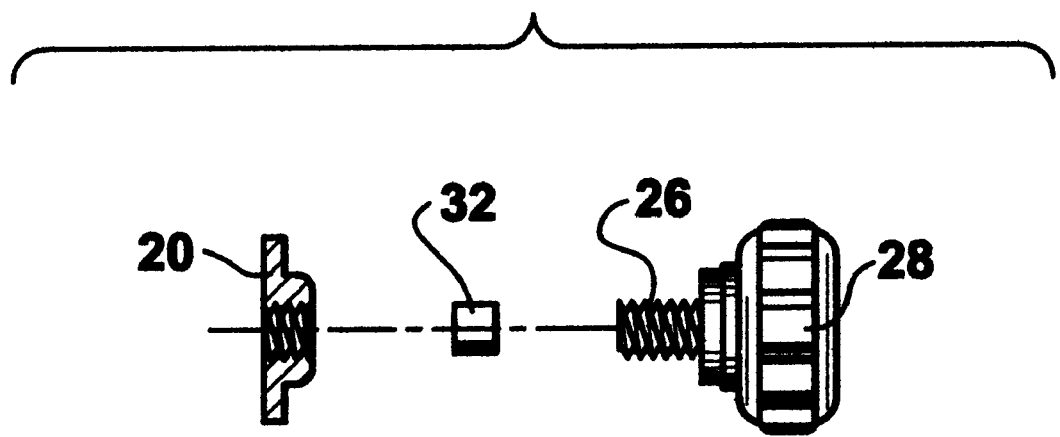
FIG. 4 is a detailed side view of one embodiment of the present invention of a part of the holding portion of the present invention having an insert.

Referring to FIG. 4, holding portion 20 of glove removal apparatus 100 is optionally comprised of a threaded insert 32 that is sufficiently secured in a portion of holding portion 20 for use with screw portion 26. Thus, in a more preferred embodiment of the invention, screw portion 26 threads through threaded insert 32 that is sufficiently secured in a portion of holding portion 20.

The present invention is manufactured from or comprised of any material or combination thereof suitable for use in the present invention. In one embodiment of the invention, the invention is comprised of a metal such as aluminum or steel. In another embodiment of the invention, the metal has a coating such as a polymer or plastic coating. In other embodiments, the apparatus of the present invention is manufactured from or comprised of carbon fiber or fiberglass. In preferred embodiments of the invention, the invention is comprised of a polymer or plastic. Polymers or plastics suitable for use with the present invention will be apparent to those skilled in the art and include, but are not limited to, polyurethane and PVC. More preferably, the apparatus of the present invention is manufactured from or comprised of a plastic capable of injection molding, such as a thermoplastic. Suitable thermoplastics include, but are not limited to, polypropylene, polyethylene, polycarbonate, thermoplastic rubber, nylons and derivatives of nylon and polystyrene. More preferably, glass-filled nylon is used. Most preferably glass-filled nylon comprising 25–40% glass is used. In embodiments of the invention comprising threaded insert 32, the insert is preferably comprised of a metal such as aluminum, brass or steel.

Any color or combination thereof may used as the material of or the covering of the present invention. As the apparatus of the present invention may be used by paramedics, law enforcement personnel and hazardous waste handlers, in a preferred embodiment of the invention, the apparatus is comprised of a red material or material with a red coating to connote the suitability of use of the present invention in emergency situations.

The present invention may be manufactured by any suitable method for fabricating the invention. The particular method of manufacture will be apparent to those skilled in the art, and will depend, in part, on the desired material of the apparatus as a finished product. Suitable methods include, but are not limited to, metal fabrication, vacuum forming and injection molding processes. In embodiments of the invention where the apparatus is comprised of a thermoplastic, the method of manufacture preferably includes the process of injection molding.

In certain embodiments of the invention, one feature of the present invention is the possibility of infection control to prevent cross-contamination. For example, the glove removal apparatus of the present invention may be used in sterile conditions by a glove wearer such as a surgeon. Thus, in one embodiment of the invention, the glove removal apparatus or member 10 is made sterile by autoclaving. Additionally, the glove removal apparatus or member 10 may be kept sterile for each action of glove removal by autoclaving the glove removal apparatus or member 10, or of any portion thereof, between uses.

Figure 5:
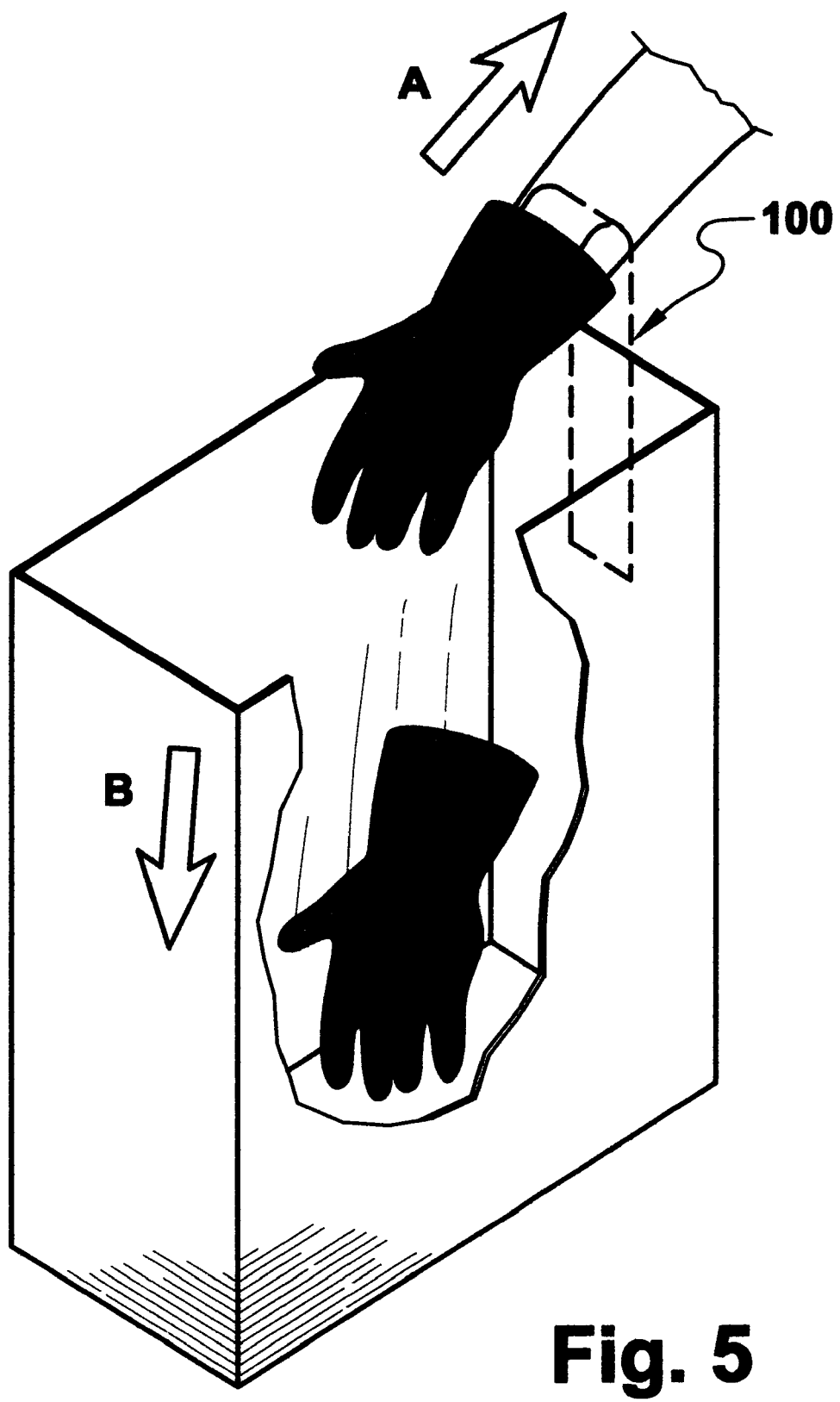
FIG. 5 illustrates an embodiment of the present invention wherein a wearer is in the process of glove removal by placing the apparatus between a glove and the forearm or wrist of the wearer, pulling away from the apparatus and allowing the glove to spring away from the apparatus and wearer and be disposed of in one step.

The operation of an embodiment of the invention will now be described. Referring to FIG. 5, glove removal apparatus 100 is shown in operation where a wearer is shown in the process of removing a potentially contaminated glove and disposing of it in one step, wherein the exterior surface of the glove does not come into physical contact with the wearer, thus preventing cross-contamination between the wearer's glove and the wearer or other personnel. In particular, member 10 of the glove removal apparatus is attached to a disposal unit through holding portion 20 and optionally secured by securer 24 to the disposal unit. The wearer uses the glove removal apparatus 100 to remove a potentially contaminated glove by inserting first end portion 18 of member 10 between the cuff of the glove and the wrist or forearm of the wearer. As the wearer moves his or her hand and arm in direction A with first end portion 18 between the glove and the wearer's hand, middle portion 12 also wedges between the glove and the wearer's palm. As the wearer continues to move his or her hand and arm in direction A and first end portion 18 comes closer towards or in contact with the fingers of the wearer, the glove begins dislodging from the wearer and the glove may start to gather around bent portion 16. Further movement of the wearer's hand and arm in direction A causes the glove to become entirely dislodged from the wearer's hand and spring off in direction B into the stationary disposal unit, away from the glove removal apparatus 100 and the wearer. Apparatus 100 substantially does not come into contact with the exterior surface of a wearer's glove during the glove removal process.

In embodiments of the invention comprising sleeve 30, sleeve 30 is used to further prevent the possibility of cross-contamination between the exterior surface of a wearer's glove and the wearer during a glove removal process and subsequent glove removals. Before each action of glove removal, a sleeve 30 may be placed over any portion, or all, of first end portion 18, middle portion 12 and bent portion 16. Sleeve 30 is kept in place on apparatus 10 by any suitable means, including friction against any part of apparatus 10 or an adhesive. Preferably, when sleeve 30 is used with the present invention, sleeve 30 extends over a part of bent portion 16 and is kept in place by friction against middle portion 12 and bent portion 16.

In one embodiment of the invention, sleeve 30 remains on member 10 for a series of glove removals. Sleeve 30 may then be removed and another sleeve placed over a portion of member 10 if desired. For example, sleeve 30 may be replaced after a series of uses by one glove wearer, at shift changes, or be replaced daily.

In a preferred embodiment, it is a feature of the present invention that when sleeve 30 is used during the glove removal process, sleeve 30 will be disposed along with the glove of a wearer. Thus, when a wearer uses the glove removal apparatus of the present invention to remove a potentially contaminated glove, sleeve 30 is also inserted between the glove of a wearer and the forearm, wrist or palm of a wearer as the wearer moves his or her hand and arm in direction A during the glove removal process as described above. Further, when continued movement of a wearer's hand or arm in direction A causes the glove to become dislodged from the wearer's hand and spring off in direction B, sleeve 30 also becomes dislodged from member 10 and is disposed of along with the wearer's glove. Preferably, a new sleeve 30 is then placed on member 10 for each action of glove removal.

The glove removal apparatus of the present invention is suitable for any application where a glove wearer desires to easily remove a glove without the assistance of the wearer's opposite hand or another person. Additionally, the apparatus of the present invention is suitable for any use to prevent cross-contamination from the exterior surface of a potentially contaminated glove and the wearer or other personnel during the glove removal process. As described above, when using the apparatus of the present invention to assist in the removal of a glove, the wearer's opposite hand, as well as other personnel, need not come into contact with the exterior surface of the glove being removed. Thus, in any situation where a glove wearer may potentially handle infectious, hazardous, offensive or harmful material, the present invention may be used to prevent cross-contamination between the exterior surface of the glove and the wearer or other personnel. For example, the latex elastomeric gloves routinely worn by dentists, surgeons, paramedics and other medical workers, laboratory technicians, hazardous waste handlers, automotive mechanics, sports trainers, and law enforcement personnel, may be easily removed with assistance of the apparatus of the present invention.

An additional feature of the present invention is that it may be placed in a location convenient for the wearer during the glove removal process and for disposal. In particular, the glove removal apparatus of the present invention may be placed over the lip of a waste receptacle, with or without holding portion 20 or be attached directly on the inside of a waste receptacle at second end portion 14 through connector 22. Additionally, the glove removal apparatus of the present invention may be attached to a wall or other stationary object at second end portion 14 or holding portion 20 substantially directly above a waste receptacle, so that when a wearer removes a glove using the glove removal apparatus of the present invention, the glove springs off in direction B into a waste receptacle.

Additionally, the glove removal device of the present invention may be mounted in the trunk or other portion of a vehicle for the convenience of glove removal by law enforcement personnel, paramedics and other safety and emergency personnel.

Various modifications of the apparatus and method of the invention in addition to those shown and described herein will become apparent to those skilled in the art from the foregoing description and fall within the scope of the following claims.

What is claimed is:

1. A glove removal apparatus adapted for the removal of a glove from a wearer's hand comprising:

a glove removing member having a first end portion, a middle portion, a bent portion, and a second end portion;

wherein, the first end portion and the middle portion are specifically adapted for insertion between said glove and said wearer's hand;

wherein, upon said glove being inserted into the apparatus, the middle portion and bent portion cooperate to remove said glove from said wearer's hand when said wearer's hand moves in a direction away from said apparatus and further comprising a sleeve adapted for fitting over at least a portion of said glove removing member.

2. A glove removal apparatus adapted for the removal of a glove from a wearer's hand comprising:

a glove removing member having a first end portion, a middle portion, a bent portion, and a second end portion;

wherein, the first end portion and the middle portion are specifically adapted for insertion between said glove and said wearer's hand;

wherein, upon said glove being inserted into the apparatus, the middle portion and bent portion cooperate to remove said glove from said wearer's hand when said wearer's hand moves in a direction away from said apparatus;

and further comprising a holding portion substantially connected with said second end portion, wherein the holding portion further comprises a securer for securing said apparatus to a stationary object wherein said securer further comprises a screw portion and a knob portion, wherein said knob portion is capable of turning so that said screw portion may be attached to a stationary object.

3. A glove removal apparatus adapted for the removal of a glove from a wearer's hand comprising:

a glove removing member having a first end portion, a middle portion, a bent portion, and a second end portion;

wherein, the first end portion and the middle portion are specifically adapted for insertion between said glove and said wearer's hand;

wherein, upon said glove being inserted into the apparatus, the middle portion and bent portion cooperate to remove said glove from said wearer's hand when said wearer's hand moves in a direction away from said apparatus;

and further comprising a holding portion substantially connected with said second end portion, wherein said holding portion is further comprised of a threaded insert sufficiently secured in said holding portion capable of receiving a threaded object whereby the threaded object is threaded through said insert for securing said apparatus to a stationary object.

4. A method of using a glove removal apparatus adapted for the removal of a glove from a wearer's hand comprising a glove removing member having a first end portion, a middle portion, a bent portion, and a second end portion, comprising:

inserting said first end portion between a portion of said glove and the wrist or forearm of the wearer, moving said hand in a direction away from said first end portion, thereby also inserting said middle portion between said glove and said wearer's hand until said glove dislodges from said wearer.

5. The method of claim 4, said glove removal apparatus further comprising a sleeve adapted for fitting over at least a portion of said glove removing member.

6. The method of claim 4, said glove removal apparatus further comprising a holding portion substantially connected with said second end portion.

7. The method of claim 6, wherein said holding portion is connected with said second end portion by a securer for attaching to a stationary object.

8. The method of claim 6, wherein said member and said holding portion are one continuous piece.

9. The method of claim 6, wherein the holding portion further comprises a securer for securing said apparatus to a stationary object.

10. The method of claim 9, wherein said securer further comprises a screw portion and a knob portion, wherein said knob portion is capable of turning so that said screw portion may be attached to a stationary object.

11. The method of claim 6, wherein said holding portion is further comprised of a threaded insert sufficiently secured in said holding portion capable of receiving a threaded object whereby the threaded object is threaded through said insert for securing said apparatus to a stationary object.

* * * * *